(12) United States Patent
Takekoshi et al.

(10) Patent No.: US 6,190,679 B1
(45) Date of Patent: Feb. 20, 2001

(54) COSMETIC COMPOSITION

(75) Inventors: Yoichiro Takekoshi; Ichiro Matsuura, both of Tokyo (JP)

(73) Assignee: Kyowa Hakko Kogyo Co., Ltd., Tokyo (JP)

( * ) Notice: Under 35 U.S.C. 154(b), the term of this patent shall be extended for 0 days.

(21) Appl. No.: 09/270,009

(22) Filed: Mar. 16, 1999

(30) Foreign Application Priority Data

Mar. 24, 1998 (JP) .................................................. 10-075624

(51) Int. Cl.⁷ ............................. A61K 7/00; A61K 7/027; A61K 7/031; A61K 7/06; A61K 7/40
(52) U.S. Cl. ............................... 424/401; 424/49; 424/59; 424/63; 424/64; 424/69; 424/70.1; 424/70.6; 424/70.7; 514/506; 514/844; 514/865; 514/846; 514/847; 514/880; 514/881
(58) Field of Search ................................. 424/401, 49, 59, 424/63, 64, 69, 70.1, 70.6, 70.7; 514/78, 506, 844–848, 880, 881

(56) References Cited

FOREIGN PATENT DOCUMENTS

| | | |
|---|---|---|
| 0 255 937 | 2/1988 | (EP) . |
| 0 719 541 | 7/1996 | (EP) . |
| 61-112007 | 5/1986 | (JP) . |
| 63-41411 | 2/1988 | (JP) . |
| 63-051930 | 3/1988 | (JP) . |
| 92 21323 | 12/1992 | (WO) . |

OTHER PUBLICATIONS

Journal of the American Oil Chemists, vol. 48. No. 11, Nov. 1971 (1971–11), pp. 697–699.

*Primary Examiner*—Gollamudi S. Kishore
(74) *Attorney, Agent, or Firm*—Fitzpatrick, Cella, Harper & Scinto

(57) ABSTRACT

A composition for cosmetics use which comprises a lysophospholipid mixture, wherein 30 mol % or more of fatty acids bonded to said lysophospholipid mixture are monoenoic fatty acids; and a cosmetic composition which comprises a lysophospholipid mixture and a cosmetically acceptable carrier, wherein 30 mol % or more of fatty acids bonded to said lysophospholipid mixture are monoenoic fatty acids. The cosmetic composition having such a lysophospholipid mixture has high storage stability and is excellent in feeling upon use.

17 Claims, No Drawings

COSMETIC COMPOSITION

FIELD OF THE INVENTION

This invention relates to lysophospholipids for use in cosmetics having high storage stability and excellent in feeling upon use as well as to a cosmetic composition comprising the same.

BACKGROUND OF THE INVENTION

Phospholipid is known as a surface active agent or emulsifying agent which is mild to the skin. Lysophospholipid obtained by converting the phospholipid into its lyso form by enzyme treatment or the like means is also known as a surface active agent or emulsifying agent which is tender to the skin (JP-A-61-112007, JP-A-63-41411; the term "JP-A" as used herein means a "Japanese published unexamined patent application"). Examples of the known lysophospholipid include those which are produced from phospholipid of animal origin such as the egg yolk, bovine brain or swine brain or from phospholipid of plant origin such as soybean, corn, rapeseed or the like plant seed, and they are used in cosmetics, quasi drugs, toiletries and the like, as surface active agents, solubilizing agents, emulsifying agents, gelling agents, moisture-keeping agents or liposome-making agents.

Since lysophospholipid, when compounded in cosmetics, can provide the products with a soft touch, it is an effective material for improving the touch of products during and after their use.

However, since there are problems from the viewpoint of stability (such as odor and discoloration), there is a limitation, in terms of formulation designing such as blending amount and masking of an oxidized soybean-like odor. Although a hydrogenated lysolecithin is available (in which unsaturated fatty acids of lysophospholipid are hydrogenated) in order to improve stability, the material provides poor feel because of less adaptability and moist sensation on the skin.

The object of the present invention is to provide lysophospholipids for use in cosmetics having both high storage stability and excellent feeling upon use, a cosmetic composition comprising the same and methods using the lysophospholipid.

SUMMARY OF THE INVENTION

The inventors of the present invention have found that cosmetics having excellent stability and feeling upon use can be obtained by preparing cosmetic compositions with lysophospholipid obtained by converting high oleic phospholipid into its lyso form.

The present invention relates to the following (1) to (14).

(1) A composition comprising lysophospholipids, wherein at least 30 mol % of the fatty acids bonded to said lysophospholipids are monoenoic fatty acids.

(2) The composition according to (1), wherein at least 50 mol % of the fatty acids bonded to said lysophospholipids are monoenoic fatty acids.

(3) The composition according to (2), wherein at least 70 mol % of the fatty acids bonded to said lysophospholipids are monoenoic fatty acids.

(4) The composition according to any one of (1) to (3), wherein at most 20 mol % of the fatty acids bonded to said lysophospholipids are polyenoic fatty acids.

(5) The composition according to (4), wherein at most 15 mol % of the fatty acids bonded to said lysophospholipids are polyenoic fatty acids.

(6) The composition according to (5), wherein at most 10 mol % of the fatty acids bonded to said lysophospholipids are polyenoic fatty acids.

(7) The composition according to any one of (1) to (6), wherein said monoenoic fatty acids have 4–34 carbon atoms.

(8) The composition according to (7), wherein said monoenoic fatty acids have 14–24 carbon atoms.

(9) The composition according to any one of (1) to (8), wherein saturated fatty acids bonded to said lysophospholipids have 1–34 carbon atoms.

(10) The composition according to (9), wherein saturated fatty acids bonded to said lysophospholipids have 6–24 carbon atoms.

(11) A cosmetic composition, which comprises the composition according to any one of (1) to (10) and a cosmetically acceptable carrier.

(12) A method of improving storage stability in a cosmetic composition, which comprises the step of blending lysophospholipids according to any one of (1) to (10) into a cosmetic composition comprising cosmetically acceptable carrier, wherein said lysophospholipids are present in said cosmetic composition in a total amount of 0.01 to 99.99% by weight.

(13) A method of improving feeling upon use of a cosmetic composition, which comprises the step of blending lysophospholipids according to any one of (1) to (10) into a cosmetic composition comprising cosmetically acceptable carrier, wherein said lysophospholipids are present in said cosmetic composition in a total amount of 0.01 to 99.99% by weight.

(14) A method of providing suitable feeling upon use of a cosmetic composition, which comprises the step of applying lysophospholipids according to any one of (1) to (10) to the body, wherein said lysophospholipids are present in said cosmetic composition in a total amount of 0.01 to 99.99% by weight.

DETAILED DESCRIPTION OF THE INVENTION

The lysophospholipid of the present invention is glycerol-based. In this event, the lysophospholipid may be either 1-acyl-2-lysophospholipid or 2-acyl-1-lysophospholipid or a mixture thereof.

Kinds of the phospholipid are not particularly limited, and examples thereof include phosphatidylcholine, phosphatidylethanolamine, phosphatidylinositol, phosphatidic acid, phosphatidylglycerol, N-acylphosphatidylethanolamine, phosphatidylserine and the like which may be used alone or as a mixture thereof.

Preferred examples of the phospholipid to be used in the present invention include phosphatidylcholine, phosphatidylethanolamine, phosphatidylinositol and phosphatidic acid.

Regarding the fatty acids bonded to the lysophospholipid mixture, those in which 30 mol % or more of the total fatty acids are monoenoic fatty acids are desirable, 50 mol % or more are monoenoic fatty acids are more desirable and 70 mol % or more are monoenoic fatty acids are most desirable.

The remaining fatty acids are saturated fatty acids and polyenoic fatty acids. Regarding the fatty acids bonded to the lysophospholipid mixture to be used in the present invention, those in which 30 mol % or more of the total fatty acids are monoenoic fatty acids and the polyenoic fatty acid content is 20 mol % or less are desirable, 30 mol % or more of the total fatty acids are monoenoic fatty acids and the polyenoic fatty acid content is 15 mol % or less are more desirable and 30 mol % or more of the total fatty acids are monoenoic fatty acids and the polyenoic fatty acid content is 10 mol % or less are most desirable.

The monoenoic fatty acid is a fatty acid which has one double bond in the alkyl chain moiety of a saturated fatty acid. Though the number of its carbon atoms is not particularly limited, straight or branched monoenoic fatty acids having 4 to 34 carbon atoms can be exemplified, and monoenoic fatty acids having 14 to 24 carbon atoms are desirable. Illustrative examples of the monoenoic fatty acid include butenoic acid, pentenoic acid, hexenoic acid, heptenoic acid, octenoic acid, nonenoic acid, decenoic acid, undecenoic acid, dodecenoic acid, tridecenoic acid, tetradecenoic acid, pentadecenoic acid, hexadecenoic acid, heptadecenoic acid, octadecenoic acid, nonadecenoic acid, icosenoic acid, henicosenoic acid, docosenoic acid, tricosenoic acid, tetracosenoic acid, pentacosenoic acid, hexacosenoic acid, heptacosenoic acid, octacosenoic acid, nonacosenoic acid, triacontenoic acid, hentriacontenoic acid, dotriacontenoic acid, tritriacontenoic acid, tetratriacontenoic acid and the like.

The decenoic acid includes obtusilic acid and the like, the dodecenoic acid includes linderic acid and the like, the tetradecenoic acid includes tsuzuic acid and the like, the hexadecenoic acid includes palmitoleic acid and the like and the octadecenoic acid includes petroselinic acid, oleic acid, elaidic acid, vaccenic acid and the like.

Any fatty acid may be used as the monoenoic fatty acid, with the proviso that it has one double bond, and it may be used as a single monoenoic fatty acid or as a mixture of monoenoic fatty acids having different carbon numbers or, even in the case of the same number of carbon atoms, monoenoic fatty acids having different position of the double bond. Oleic acid is desirable as the monoenoic fatty acid.

Regarding the fatty acid bonded to the lysophospholipid mixture to be used in the present invention, any fatty acid may be bonded, with the proviso that it satisfies the aforementioned conditions.

With respect to the saturated fatty acid, the number of carbon atoms is not particularly limited, and straight or branched saturated fatty acids having 1 to 34 carbon atoms can be exemplified, of which saturated fatty acids having 6 to 24 carbon atoms are desirable. Illustrative examples of the saturated fatty acid include formic acid, acetic acid, propionic acid, butanoic acid (butyric acid), pentanoic acid, hexanoic acid (caproic acid), heptanoic acid, octanoic acid (caprylic acid), nonanoic acid, decanoic acid (capric acid), undecanoic acid, dodecanoic acid (lauric acid), tridecanoic acid, tetradecanoic acid (myristic acid), pentadecanoic acid, hexadecanoic acid (palmitic acid), heptadecanoic acid (margaric acid), octadecanoic acid (stearic acid), nonadecanoic acid, icosanoic acid (arachidic acid), henicosanoic acid, docosanoic acid (behenic acid), tricosanoic acid, tetracosanoic acid (lignoceric acid), pentacosanoic acid, hexacosanoic acid (cerotic acid), heptacosanoic acid, octacosanoic acid (montanoic acid), nonacosanoic acid, triacontanoic acid (melissic acid), hentriacontanoic acid, dotriacontanoic acid, tritriacontanoic acid, tetratriacontanoic acid and the like.

The polyenoic fatty acid is a fatty acid which has two or more double bonds in the alkyl chain moiety of a saturated fatty acid, and its examples include a dienoic fatty acid which has two double bonds in the alkyl chain moiety of a saturated fatty acid and a trienoic fatty acid which has three double bonds in the alkyl chain moiety of a saturated fatty acid. The position of double bonds in the alkyl moiety of the polyenoic fatty acid is not particularly limited.

Illustrative examples of the dienoic fatty acid include straight or branched fatty acid having 6 to 34 carbon atoms such as hexadienoic acid, heptadienoic acid, octadienoic acid, nonadienoic acid, decadienoic acid, undecadienoic acid, dodecadienoic acid, tridecadienoic acid, tetradecadienoic acid, pentadecadienoic acid, hexadecadienoic acid, heptadecadienoic acid, octadecadienoic acid, nonadecadienoic acid, icosadienoic acid, henicosadienoic acid, docosadienoic acid, tricosadienoic acid, tetracosadienoic acid, pentacosadienoic acid, hexacosadienoic acid, heptacosadienoic acid, octacosadienoic acid, nonacosadienoic acid, triacontadienoic acid, hentriacontadienoic acid, dotriacontadienoic acid, tritriacontadienoic acid, tetratriacontadienoic acid and the like. The octadecadienoic acid includes linoleic acid.

Illustrative examples of the trienoic fatty acid include straight or branched fatty acids having 8 to 34 carbon atoms such as octatrienoic acid, nonatrienoic acid, decatrienoic acid, undecatrienoic acid, dodecatrienoic acid, tridecatrienoic acid, tetradecatrienoic acid, pentadecatrienoic acid, hexadecatrienoic acid, heptadecatrienoic acid, octadecatrienoic acid, nonadecatrienoic acid, icosatrienoic acid, henicosatrienoic acid, docosatrienoic acid, tricosatrienoic acid, tetracosatrienoic acid, pentacosatrienoic acid, hexacosatrienoic acid, heptacosatrienoic acid, octacosatrienoic acid, nonacosatrienoic acid, triacontatrienoic acid, hentriacontatrienoic acid, dotriacontatrienoic acid, tritriacontatrienoic acid, tetratriacontatrienoic acid and the like. The octadecatrienoic acid includes, for example, γ-linolenic acid and α-linolenic acid.

Fatty acids having four or more double bonds, such as arachidonic acid, eicosapentaenoic acid, docosahexaenoic acid and the like, can also be exemplified as the polyenoic acid.

The fatty acid to be bonded to the lysophospholipid may be substituted by one to four hydroxy groups or one or two oxy groups.

The lysophospholipid to be used in the present invention can be produced by synthesis, but it is desirable to produce it by enzymatically hydrolyzing an acyl group at a specific site of natural phospholipid or synthesized phospholipid with phospholipase $A_1$ or phospholipase $A_2$. As the phospholipid, natural phospholipid is desirable because it can be obtained with a low cost. The phospholipid may be used by modifying it in advance by its treatment with phospholipase D or the like enzyme, or by fractionating its specific components using a solvent or the like.

It is desirable that, after the enzyme treatment, the lysophospholipid to be used in the present invention is purified by further treating it with acetone, methanol, ethanol, propanol, isopropanol and the like organic solvents.

Animal or plant phospholipid can be exemplified as the natural phospholipid. Examples of the plant phospholipid include those which are obtained from high oleic safflower, high oleic corn, lauric acid rich rapeseed and the like. As other sources of phospholipid, it is possible to use a plant phospholipid whose fatty acid composition is modified to the aforementioned composition for example by genetic recombination techniques. Egg yolk phospholipid can be exemplified as the animal phospholipid. The lysophospholipid to be used in the present invention is obtained preferably by enzymatically treating a natural phospholipid mixture containing 30 mol % or more of monoenoic fatty acid with the aforementioned phospholipase, more preferably by enzymatically treating a natural phospholipid mixture containing 30 mol % or more of monoenoic fatty acid and 20 mol % or less of polyenoic fatty acid with the aforementioned phospholipase.

Isolation of phospholipid from an animal or plant material can be made by any method. For example, the gum formed by adding water to crude oil at the degumming step during the process of plant oil production can be used.

Examples of the cosmetics of the present invention include toilet soaps, cleansing articles, shampoos, rinses, hairdyes, hair cosmetics, creams, milky lotions, face lotion, face oils, sunburn/suntan oils, face powders/powders, packs, nail creams, cheek rouges, eyebrow pencils, eye creams, eye shadows, mascara articles, lipsticks, lip creams, dental creams, bathing cosmetics and the like.

Though not particularly limited, examples of the body part to which the cosmetics of the present invention are applied include head hair, body hair, skin, face, lips, mouth and the like.

When the cosmetics of the present invention are applied to the body, excellent feeling upon use such as softness, spreading touch or conformability is obtained during their use, and excellent feeling upon use such as moistness or refreshment is obtained after their use.

The cosmetic of the present invention comprises lysophospholipid and a carrier acceptable for cosmetics. The lysophospholipid content is from 0.001 to 99.99% by weight, preferably from 0.01 to 50% by weight, more preferably from 0.1 to 5% by weight.

Examples of the carrier include those materials which are generally used in cosmetics and pharmaceutical preparations, such as oils and fats, hydrocarbons, waxes, fatty acids, synthetic esters, alcohols, surface active agents, thickeners, moisture-keeping agents, antiseptics, antioxidants, pH adjusting agents, perfumes, pigments, drugs, purified water and the like, and these carriers may be used alone or as a mixture of two or more.

These carriers, alone or as a mixture of two or more, may be used in an amount of from 0.001 to 99.99% by weight, preferably from 50 to 99.99% by weight, more preferably from 95 to 99.5% by weight.

Examples of the oils and fats include jojoba oil, castor oil, olive oil, soybean oil, palm oil, cacao butter, camellia oil, coconut oil, Japan wax, grape seed oil, avocado oil, yolk oil, minke whale oil, turtle oil and the like.

Examples of the hydrocarbons include liquid paraffin, vaseline, microcrystalline wax, ceresin wax, paraffin wax, squalane, α-olefin oligomer and the like.

Examples of the waxes include beeswax, lanolin, carnauba wax, candelilla wax, whale wax and the like.

Examples of the fatty acids include lauric acid, myristic acid, palmitic acid, stearic acid, oleic acid, isostearic acid, behenic acid and the like.

Examples of the synthetic esters include cetyl palmitate, isopropyl myristate, isopropyl palmitate, butyl oleate, octyldodecyl oleate, cholesterol oleate, myristyl myristate, octyldecyl myristate, propylene glycol monostearate, myristyl lactate, isostearyl malate, glycerol monostearate, distearyl dimethyl ammonium chloride and the like.

It is desirable that each of oils and fats, hydrocarbons, waxes, fatty acids and synthetic esters is blended to a ratio of from 0 to 70% by weight.

Examples of the alcohols include ethanol, 1,3-butylene glycol, propylene glycol, lauryl alcohol, cetanol, hexyl decanol, octyl dodecanol, stearyl alcohol, oleyl alcohol and the like. These alcohols are blended at a ratio of from 0 to 60% by weight.

Examples of the surface active agents include decaglycerol monomyristate or the like lipophilic glycerol fatty acid ester, self emulsification-type glycerol fatty acid ester, polyglycerol fatty acid ester, polyoxyethylene glycerol fatty acid ester, polyoxyethylene hydrogenated castor oil, polyoxyethylene sorbitol fatty acid ester, polyoxyethylene (20) cetyl ether or the like polyoxyethylene alkyl ether, sodium polyoxyethylene fatty acid ester alkylsulfate, sodium polyoxyethylene alkylsulfate, sodium alkylbenzenesulfonate, polyoxyethyleneglyceryl pyroglutamate isostearate, dialkyl sulfosuccinate, cetyl pyridinium bromide, n-octadecyltrimethylammonium chloride, monoalkylphosphoric acid, N-acylglutamic acid, polyoxyethylene reduced lanolin and the like. It is desirable to blend these surface active agents at a ratio of from 0 to 40% by weight.

Examples of the thickeners include sodium alginate, xanthan gum, aluminum silicate, carboxyvinyl polymer, polyvinyl alcohol, methyl polysiloxane, dextran, carboxymethylcellulose, carrageenan, hydroxypropylmethylcellulose, soluble starch, cationated cellulose, tragacanth gum, quince seed extract and the like. It is desirable to blend these thickeners at a ratio of from 0 to 0.5% by weight.

Examples of the moisture-keeping agents include glycerol, propylene glycol, 1,3-butylene glycol, pyrrolidonecarboxylic acid, lactic acid, hyaluronic acid and the like. It is desirable to blend these moisture-keeping agents at a ratio of from 0 to 60% by weight.

Examples of the antiseptics include benzoic acid, salicylic acid or dehydroacetic acid or salts thereof, paraoxybenzoic acid ester such as methylparaben or propylparaben, triclosan halocarban, benzalkonium chloride, hinokitiol, resorcinol and the like. It is desirable to blend these antiseptics at a ratio of from 0 to 1% by weight.

Examples of the antioxidants include dibutylhydroxyltoluene, butylhydroxyanisole, propyl gallate, ascorbic acid and the like. It is desirable to blend these antioxidants at a ratio of from 0 to 5% by weight.

Examples of the pH adjusting agents include sodium hydroxide, triethanolamine, citric acid, sodium citrate, boric acid, borax, potassium hydrogenphosphate and the like. It is desirable to blend these pH adjusting agents at a ratio of from 0 to 5% by weight.

Regarding the perfumes, any perfume can be used with the proviso that it is generally used in cosmetics.

Examples of the pigments include iron oxide, titanium dioxide, zinc oxide, kaolin, talc and the like. It is desirable to blend these pigments at a ratio of from 0 to 90% by weight.

Examples of the drugs include wheat germ oil, vitamin E, vitamin A, vitamin $B_2$, ascorbic acid 2-phosphate magnesium salt, D-pantothenyl alcohol, dipotassium glycyrrhetinate, glutathione and the like. It is desirable to blend these drugs at a ratio of from 0 to 5% by weight.

TEST EXAMPLE 1

An organoleptic test was carried out using the face lotions produced in Example 1 and Comparative Example 1.

Softness and spreading/conformability during their use and moistness after use were evaluated as organoleptic characteristics by 10 cosmetics panels. The evaluation was carried out by a five point method, and the results were expressed as average values. The results are shown in Table 1.

TABLE 1

| Items evaluated | | | Example 1 | Comparative Example 1 |
|---|---|---|---|---|
| Organoleptic characteristics | During use | Softness | 5 | 2 |
| | | Spreading/conformability | 5 | 2 |
| | After use | Moistness | 5 | 3 |

The hydrogenated soybean lysophospholipid showed inferior softness and spreading/conformability during use and moistness after use when compared with the soybean lysophospholipid which, therefore, was excellent in feeling upon use.

TEST EXAMPLE 2

Organoleptic characteristics and emulsifying stability were evaluated using the face lotions produced in Example 1 and Comparative Example 2.

Softness and spreading touch during their use and refreshing feeling after use were evaluated as organoleptic characteristics by 10 cosmetics panels. The evaluation was carried out by a five point method, and the results were expressed as average values. The odor was judged as "good" when it did not change, "slightly good" when slightly changed or "bad" when markedly changed.

The storage stability test was carried out by an organoleptic inspection and an instrumental analysis after 1 to 2 weeks of storage of each sample at 5° C. or 40° C. or under UV irradiation (light source: BBL; FL20S-BL-B manufactured by Matsushita Electric Works, 20 cm in irradiation distance, room temperature) or sunlight irradiation.

Characteristics of the appearance were observed, and the results were judged as "good" when no changes were found, "slightly good" when slight changes were found or "bad" when significant changes were found.

Changes in color tone were evaluated using samples stored under UV irradiation or at 40° C., by measuring color differences from samples stored at room temperature. As the colorimeter, SE 2000 (Japan Denshoku Kogyo) was used.

The results are shown in Table 2.

TABLE 2

| Items tested | | Example 1 | Comparative Example 2 |
|---|---|---|---|
| Emulsification stability | | | |
| | 5° C. | good | good |
| | Room temperature | good | slightly good |
| | 40° C. | good | bad |
| | UV irradiation | slightly good | bad |
| Organoleptic characteristics | | | |
| Odor | 5° C. | good | slightly good |
| | 40° C. | slightly good | bad |

TABLE 2-continued

| Items tested | | Example 1 | Comparative Example 2 |
|---|---|---|---|
| | UV irradiation | good | bad |
| During use | Softness | 5 | 3 |
| | Spreading touch | 5 | 3 |
| After use | Refreshing feeling | 5 | 1 |
| Color tone (ΔE) | Sunlight irradiation | — | — |
| | UV irradiation | 0.48 | 2.24 |

Since the soybean lysophospholipid was sensitive to high temperature and light, it showed a sticky feeling as the sense of touch, and its appearance was considerably discolored by the UV irradiation. Regarding the high oleic safflower lysophospholipid, it was stable against temperature and light, so that its organoleptic inspection resulted in excellent softness, spreading touch and refreshing feeling. Changes in color tone were not found.

TEST EXAMPLE 3

Organoleptic characteristics and emulsifying stability were evaluated using the creams produced in Example 2 and Comparative Example 3.

The storage stability test was carried out by an organoleptic inspection and an instrumental analysis after 1 to 2 weeks of storage of each sample at 5° C. or 40° C. or under UV irradiation (light source: BBL; FL20S-BL-B manufactured by Matsushita Electric Works, 20 cm in irradiation distance, room temperature) or sunlight irradiation.

Characteristics of the appearance were observed, and the results were judged as "good" when no changes were found, "slightly good" when slight changes were found or "bad" when significant changes were found.

Changes in color tone were evaluated using samples stored under UV irradiation or at 40° C., by measuring color differences from samples stored at room temperature. As the calorimeter, SE 2000 (Japan Denshoku Kogyo) was used.

The results are shown in Table 3.

TABLE 3

| Items tested | | Example 2 | Comparative Example 3 |
|---|---|---|---|
| Emulsification stability | | | |
| | 5° C. | good | good |
| | Room temperature | good | slightly good |
| | 40° C. | good | bad |
| | UV irradiation | slightly good | bad |
| Organoleptic characteristics | | | |
| Odor | 5° C. | 3 | 3 |
| | 40° C. | 4 | 1 |
| | UV irradiation | 5 | 1 |
| During use | Softness | 5 | 3 |
| | Spreading touch | 5 | 3 |
| After use | Refreshing feeling | 5 | 3 |
| Color tone (ΔE) | Sunlight irradiation | 1.22 | 5.97 |
| | UV irradiation | 0.27 | 1.77 |

With regard to the amount of lipid peroxide, the peroxide value was obtained by the chloroform method [*Oil*

Chemistry, 36, 276–278 (1987)], and the amount of thiobarbituric acid (TBA) reaction product was obtained by the TBA method [Journal of the Japanese Society of Scientific Fisheries, 45, 499 (1979)].

The results are shown in Table 4.

TABLE 4

| Items tested | | Example 2 | Comparative Example 3 |
|---|---|---|---|
| Peroxide value (chloroform method) (meq/kg) | Room temp. | 6.5 | 6.1 |
| | 40° C. | 8.8 | 8.3 |
| | UV irradiation | 4.8 | 17.9 |
| TBA reaction product (nmol/g) | Room temp. | 1 | 3 |
| | 40° C. | 2 | 4 |
| | UV irradiation | 2 | 10 |

Since the soybean lysophospholipid was sensitive to high temperature and light, a sticky feeling remained as the sense of touch, and its appearance was considerably discolored by the sunlight and UV irradiation.

Regarding the high oleic safflower lysophospholipid, it was stable against temperature and light, so that its organoleptic inspection resulted in excellent spreading touch and conformability. Though color tone was changed by sunlight irradiation, it was not a coloration but a color difference changed from yellow to white. Changes in color tone were not found by UV irradiation.

Being sensitive to light, the soybean lysophospholipid showed accelerated oxidation in terms of both peroxide value and amount of TBA reaction product, which coincided with the results of organoleptic test on odor and color difference in coloration. The cosmetic formulated using high oleic lysophospholipid was stable against temperature and light and therefore was superior to the conventional soybean lysophospholipid.

Examples of the present invention are given below by way of illustration and not by way of limitation.

EXAMPLE 1

The contents of the following component (A) were mixed and dissolved and warmed up to 60° C., and the contents of the following component (B) mixed and dissolved at 55° C. in advance were added to the component (A) and uniformly dissolved therein to produce a face lotion having the following composition. In this case, the high oleic safflower lysophospholipid produced in Example 3 was used. The amount of each compound was shown by % by weight.

| (A) | Methylparaben (mfd. by Midori Kagaku) | 0.1 |
|---|---|---|
| | 1,3-Butylene glycol | 3.0 |
| | (1,3-Butylene Glycol P, mfd. by Kyowa Yuka) | |
| | Glycerol | 1.8 |
| | (conc. glycerol, mfd. by Sakamoto Pharmaceutical) | |
| | Dipotassium glycyrrhetinate | 0.1 |
| | (Glycynon K$_2$, mfd. by Tokiwa Phytochemistry Lab.) | |
| | 1% Sodium hyaluronate | 2.0 |
| | (mfd. by Kowa Hakko Kogyo) | |
| | Purified water | 91.0 |
| (B) | High oleic safflower lysophospholipid | 0.2 |
| | Propylene glycol (mfd. by Dow Chemical) | 1.8 |

COMPARATIVE EXAMPLE 1

A face lotion was produced in the same manner as described in Example 1, except that hydrogenated soybean lysophospholipid (Hydrogenated Soybean lysophospholipid, mfd. by The Nisshin Oil Mills) was used instead of the high oleic safflower lysophospholipid.

COMPARATIVE EXAMPLE 2

A cream was produced in the same manner as described in Example 2, except that soybean phospholipid (mfd. by Kyowa Hakko Kogyo) was used instead of the high oleic safflower lysophospholipid.

EXAMPLE 2

The contents of the following component (A) were mixed and dissolved at 85° C., the contents of the following component (B) mixed and dissolved in advance at 85° C. were added to the component (A) and uniformly stirred, and then the following component (C) was added to the resulting mixture and uniformly mixed and cooled to produce a cream having the following composition. In this case, the high oleic safflower lysophospholipid produced in Example 3 was used. The amount of each compound was shown by % by weight.

| (A) | Decaglyceryl monomyristate | 1.2 |
|---|---|---|
| | (NIKKOL Decaglyn, mfd. by Nikko Chemicals) | |
| | POE (20) cetyl ether | 1.8 |
| | (EMALEX 1620, mfd. by Nippon Emulsion) | |
| | α-Olefin oligomer | 8.0 |
| | (NIKKOL Syntheran 4, mfd. by Nikko Chemicals) | |
| | Squalane (mfd. by Kishimoto Liver Oil) | 4.0 |
| | Cetyl palmitate | 3.0 |
| | (NIKKOL N-SP, mfd. by Nikko Chemicals) | |
| | Cetanol | 4.4 |
| | (Conol 30 RC, mfd. by New Japan Chemical) | |
| | Propylparaben (mfd. by Midori Kagaku) | 0.03 |
| | High oleic safflower lysophospholipid | 2.0 |
| (B) | Methylparaben (mfd. by Midori Kagaku) | 0.1 |
| | 1,3-Butylene glycol | 6.0 |
| | (1,3-Butylene Glycol P, mfd. by Kyowa Yuka) | |
| | Glycerol | 3.0 |
| | (conc. glycerol, mfd. by Sakamoto Pharmaceutical) | |
| | Purified water | 56.47 |
| (C) | 0.5% Carboxyvinyl polymer solution | 10.0 |
| | (Carbopol 980, mfd. by B. F. Goodrich) | |

COMPARATIVE EXAMPLE 3

A cream was produced in the same manner as described in Example 2, except that soybean phospholipid (mfd. by Kyowa Hakko Kogyo) was used instead of the high oleic safflower lysophospholipid.

EXAMPLE 3

A 4 ml portion of 5N sodium hydroxide aqueous solution was added to 400 g of hydrated phospholipid having a moisture content of 55% (mfd. by True Lecithin Industry) obtained from the degumming step of high oleic safflower oil and the mixture was warmed up to 50° C., and then 24 hours of lyso-conversion reaction was carried out at 50° C. by adding 0.12 ml of Lecithase (mfd. by NOVO) as a hydrolase to the stirring mixture.

Using a rotary evaporator, the reaction solution was concentrated and dehydrated with heating under a reduced pressure. Thereafter, diatomaceous earth was added to the resulting residue and the precipitate was removed using a pressure filtration apparatus, thereby obtaining an enzyme-treated phospholipid preparation.

Said treated preparation was washed with 10 volumes of acetone and dried under a reduced pressure to obtain an enzyme-treated purified phospholipid preparation (80 mol % in lyso-conversion ratio) in the form of powder.

REFERENCE EXAMPLE 1

Results of the fatty acid analysis of the high oleic safflower lysophospholipid produced in Example 3, the hydrogenated soybean lysophospholipid used in Comparative Example 1 and the soybean lysophospholipid used in Comparative Examples 2 and 3 are shown in Table 5. In this connection, the fatty acid composition was analyzed by firstly carrying out methyl esterification of each sample by the boron trifluoride-methanol method of the Standard Test Methods for Fat Analysis and then testing the resulting sample based on a flame ionization type constant temperature gas chromatography. Data in the table are shown by mol % of fatty acids.

TABLE 5

| Fatty acids | High oleic safflower lysophospholipid | Soybean lysophospholipid | Hydrogenated soybean lysophospholipid |
|---|---|---|---|
| Palmitic acid | 10.2 | 26.7 | 17 |
| Stearic acid | 1.2 | 6.2 | 57 |
| Oleic acid | 77.7 | 13.9 | 25 |
| Linoleic acid | 10.3 | 49.1 | 1 |
| Linolenic acid | 0.6 | 4.1 | N.D. |

N.D.: not detectable

As shown above, stable cosmetics having excellent feeling upon use can be provided by the present invention.

While the invention has been described in detail and with reference to specific embodiments thereof, it will be apparent to one skilled in the art that various changes and modifications can be made therein without departing from the spirit and scope thereof.

This application is based on Japanese patent application No. Hei. 10-75624, filed on Mar. 24, 1998, and incorporated herein by reference.

What is claimed is:

1. A cosmetic compositions, comprising lysophospholipids, wherein at least 30 mol % of the fatty acids bonded to said lysophospholipids are monoenoic fatty acids and at most 20 mol % of the fatty acids bonded to said lysophospholipids are polyenoic fatty acids, and a cosmetically acceptable carrier.

2. The composition according to claim 1, wherein at least 50 mol % of the fatty acids bonded to said lysophospholipids are monoenoic fatty acids.

3. The composition according to claim 2, wherein at least 70 mol % of the fatty acids bonded to said lysophospholipids are monoenoic fatty acids.

4. The composition according to any one of claims 1 to 3, wherein said monoenoic fatty acids have 4–34 carbon atoms.

5. The composition according to claims 1 to 3, wherein said monoenoic fatty acids have 14–24 carbon atoms.

6. A method of improving storage stability in a cosmetic composition, which comprises the step of blending lysophospholipids into a cosmetic composition comprising a cosmetically acceptable carrier, wherein at least 30 mol % of the fatty acids bonded to said lysophospholipids are monoenoic fatty acids and at most 20 mol % of the fatty acids bonded to said lysophospholipids are polyenoic fatty acids, and wherein said lysophospholipids are present in said cosmetic composition in a total amount of 0.01 to 50.0% by weight.

7. The method according to claim 6, wherein at least 50 mol % of the fatty acids bonded to said lysophospholipids are monoenoic fatty acids.

8. The method according to claim 7, wherein at least 70 mol % of the fatty acids bonded to said lysophospholipids are monoenoic fatty acids.

9. The method according to any one of claims 6–8 wherein said lysophospholipids are present in said cosmetic composition in a total amount of 0.1 to 5.0% by weight.

10. A method of improving feel upon use of a cosmetic composition, which comprises the step of blending lysophospholipids into a cosmetic composition comprising cosmetically acceptable carrier, wherein at least 30 mol % of the fatty acids bonded to said lysophospholipids are monoenoic fatty acids and at most 20 mol % of the fatty acids bonded to said lysophospholipids are polyenoic fatty acids, and wherein said lysophospholipids are present in said cosmetic composition in a total amount of 0.01 to 50.0% by weight.

11. The method according to claim 10, wherein at least 50 mol % of the fatty acids bonded to said lysophospholipids are monoenoic fatty acids.

12. The method according to claim 11, wherein at least 70 mol % of the fatty acids bonded to said lysophospholipids are monoenoic fatty acids.

13. The method according to any one of claims 10–12, wherein said lysophospholipids are present in said cosmetic composition in a total amount of 0.1 to 5.0% by weight.

14. A method of providing suitable feel upon use of a cosmetic composition, which comprises the step of applying lysophospholipids to the body, wherein at least 30 mol % of the fatty acids bonded to said lysophospholipids are monoenoic fatty acids and at most 20 mol % of the fatty acids bonded to said lysophospholipids are polyenoic fatty acids, and wherein said lysophospholipids are present in said cosmetic composition in a total amount of 0.01 to 50.0% by weight.

15. The method according to claim 14, wherein at least 50 mol % of the fatty acids bonded to said lysophospholipids are monoenoic fatty acids.

16. The method according to claim 15, wherein at least 70 mol % of the fatty acids bonded to said lysophospholids are monoenoic fatty acids.

17. The method according to any one of claims 14–16, wherein said lysophospholipids are present in said cosmetic composition in a total amount of 0.1 to 5.0% by weight.

* * * * *

UNITED STATES PATENT AND TRADEMARK OFFICE
CERTIFICATE OF CORRECTION

PATENT NO. : 6,190,679 B1  Page 1 of 1
DATED : February 20, 2001
INVENTOR(S) : Yoichiro Takekoshi et al.

It is certified that error appears in the above-identified patent and that said Letters Patent is hereby corrected as shown below:

Column 1,
Line 22, "quasi drugs," should read -- quasi-drugs, --.

Column 2,
Line 4, "(7)." should read -- (7) --.

Column 11,
Line 43, "compositions," should read -- composition, --.

Column 12,
Line 16, "6-8" should read -- 6-8, --;
Line 23, "comprising" should read -- comprising a --; and
Line 55, "lysophospholids" should read -- lysophospholipids --.

Signed and Sealed this

Twenty-fifth Day of December, 2001

Attest:

JAMES E. ROGAN
*Attesting Officer*  *Director of the United States Patent and Trademark Office*